US008556984B2

(12) United States Patent
 Calamel

(10) Patent No.: US 8,556,984 B2
(45) Date of Patent: Oct. 15, 2013

(54) INSERT FOR A COTYLOID IMPLANT CUP FOR A JOINT PROSTHESIS, COTYLOID IMPLANT AND JOINT PROSTHESIS

(75) Inventor: Serge Calamel, La Ciotat (FR)

(73) Assignee: Biotechni, La Ciotat (FR)

( * ) Notice: Subject to any disclaimer, the term of this patent is extended or adjusted under 35 U.S.C. 154(b) by 842 days.

(21) Appl. No.: 10/559,680

(22) PCT Filed: Jun. 7, 2004

(86) PCT No.: PCT/FR2004/001410
§ 371 (c)(1),
(2), (4) Date: Dec. 6, 2005

(87) PCT Pub. No.: WO2004/110318
PCT Pub. Date: Dec. 23, 2004

(65) Prior Publication Data
US 2006/0276905 A1 Dec. 7, 2006

(30) Foreign Application Priority Data
Jun. 6, 2003 (FR) ..................................... 03 06893

(51) Int. Cl.
*A61F 2/32* (2006.01)
(52) U.S. Cl.
USPC ....................................................... 623/22.13
(58) Field of Classification Search
USPC ............................................ 623/22.11–23.38
See application file for complete search history.

(56) References Cited

U.S. PATENT DOCUMENTS

| 3,698,017 | A | * | 10/1972 | Scales et al. | 623/22.24 |
| 3,723,995 | A | * | 4/1973 | Baumann | 623/22.16 |
| 3,818,512 | A | * | 6/1974 | Shersher | 623/22.15 |
| 3,863,273 | A | * | 2/1975 | Averill | 623/22.17 |
| 3,903,549 | A | * | 9/1975 | Deyerle | 623/22.36 |
| 3,939,497 | A | * | 2/1976 | Heimke et al. | 623/22.36 |
| 4,035,848 | A | * | 7/1977 | Wagner | 623/23.12 |
| 4,172,296 | A | * | 10/1979 | D'Errico | 623/22.28 |
| 4,180,873 | A | * | 1/1980 | Fixel | 623/22.23 |
| 4,380,090 | A | * | 4/1983 | Ramos | 623/22.2 |
| 4,408,360 | A | * | 10/1983 | Keller | 623/22.2 |
| 4,566,138 | A | * | 1/1986 | Lewis et al. | 623/22.38 |
| 4,662,891 | A | * | 5/1987 | Noiles | 623/22.31 |
| 4,678,472 | A | * | 7/1987 | Noiles | 623/23.4 |
| 4,715,859 | A | * | 12/1987 | Schelhas et al. | 623/22.27 |

(Continued)

FOREIGN PATENT DOCUMENTS

EP          0 297 789 A    1/1989
WO          WO 01/24739   4/2001

*Primary Examiner* — David Isabella
*Assistant Examiner* — Ann Schillinger
(74) *Attorney, Agent, or Firm* — Young & Thompson

(57) ABSTRACT

An acetabular implant cup insert for a joint prosthesis, the insert being of the type having a metal shell (1) and a polymer lining (14) lining the inside space (4) of the shell (1), a receptacle (18) for a prosthetic head being formed in the lining (14), the shell presenting on its inside space (4) elements for preventing the lining (14) being extracted from the shell (1) and elements for preventing the lining (14) turning in the shell (1), the insert being characterized in that the elements for preventing the lining being extracted include a stud (11) disposed on the end wall (10) of the shell (1) and presenting at least one groove (12) or lip. An acetabular implant including a cup and an insert of the above type. A joint prosthesis of the type including an acetabular implant of the above type and a prosthetic head.

17 Claims, 2 Drawing Sheets

(56) References Cited

U.S. PATENT DOCUMENTS

Figure 2:
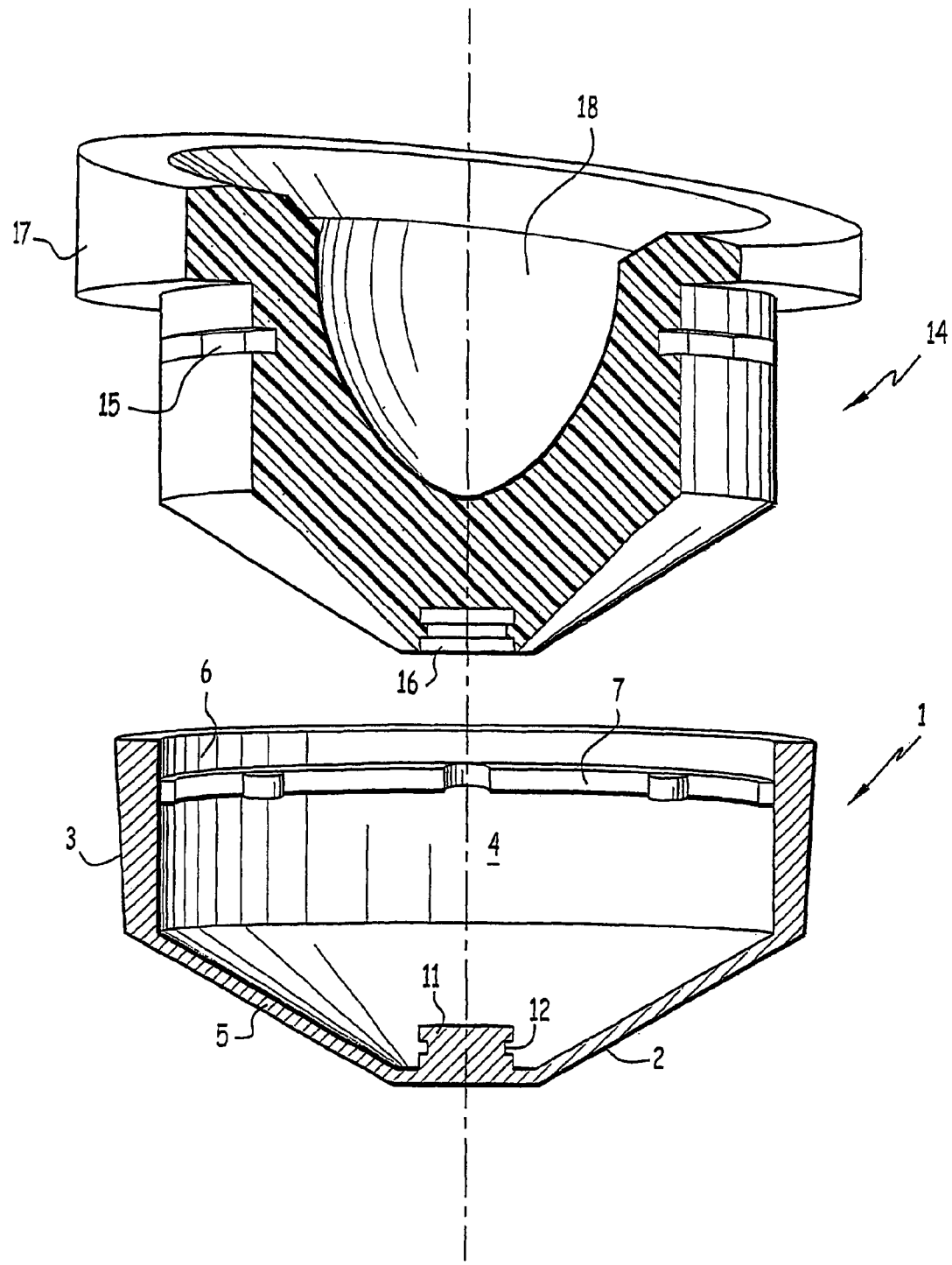

| | | | |
|---|---|---|---|
| 4,828,565 A * | 5/1989 | Duthoit et al. | 623/22.3 |
| 4,878,916 A * | 11/1989 | Rhenter et al. | 623/22.24 |
| 4,904,267 A * | 2/1990 | Bruce et al. | 128/898 |
| 4,919,674 A * | 4/1990 | Schelhas | 623/22.29 |
| 4,963,154 A * | 10/1990 | Anapliotis et al. | 623/22.28 |
| 5,002,580 A * | 3/1991 | Noble et al. | 623/23.23 |
| 5,021,062 A * | 6/1991 | Adrey et al. | 623/22.36 |
| 5,080,677 A | 1/1992 | Shelley | |
| 5,549,696 A * | 8/1996 | Willi | 623/22.28 |
| 5,645,594 A | 7/1997 | Devanathan et al. | |
| 5,645,606 A * | 7/1997 | Oehy et al. | 623/22.34 |
| 5,658,348 A * | 8/1997 | Rohr, Jr. | 623/22.29 |
| 5,735,901 A * | 4/1998 | Maumy et al. | 128/898 |
| 6,692,529 B2 * | 2/2004 | Shah | 623/22.13 |

* cited by examiner

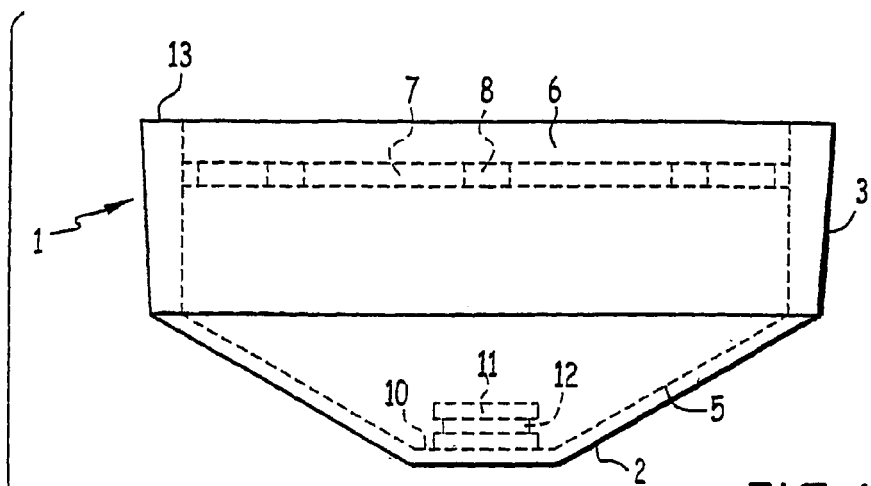
FIG.1a
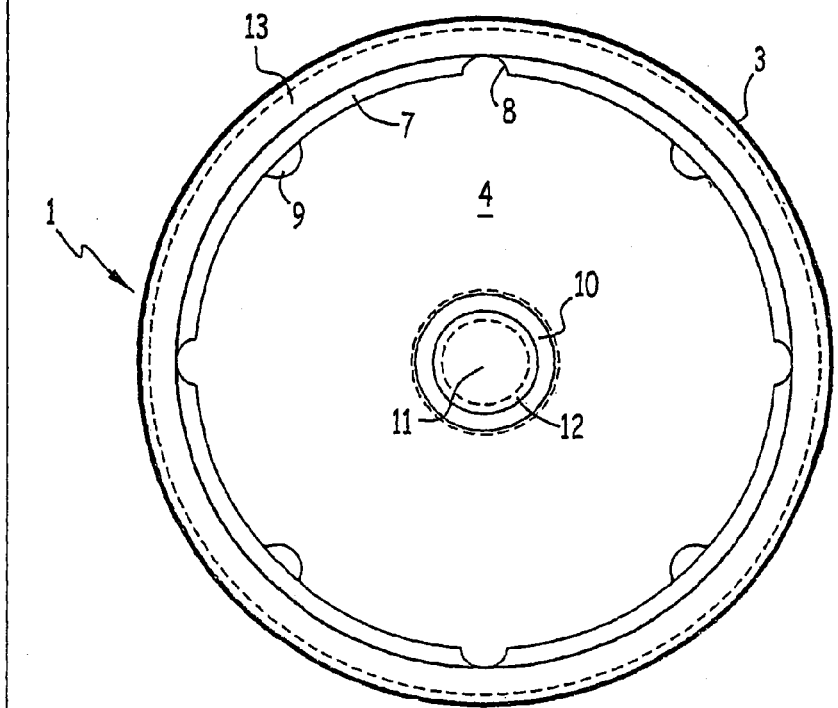
FIG.1
FIG.1b

INSERT FOR A COTYLOID IMPLANT CUP FOR A JOINT PROSTHESIS, COTYLOID IMPLANT AND JOINT PROSTHESIS

The invention relates to the field of joint prostheses, such as hip or shoulder prostheses.

It is conventional to use hip prostheses made up firstly of a metal rod with a ceramic femur head of substantially spherical shape that the surgeon substitutes for the top portion of the patient's femur, and secondly an acetabular implant for receiving said femur head and that the surgeon implants, e.g. by means of cement, in the pelvis of the patient at the location of the natural acetabulum.

In a known example of such a prosthesis, the acetabular implant comprises two parts:
  a metal cup fastened in the pelvis at the location of the natural acetabulum by means of cement or screws; and
  an insert lining the inside of the cup, for the purpose of receiving the femur head of the prosthesis and presenting a shape that matches that of the femur head.

The insert is preferably made of ceramic so as to present better resistance to wear during movements of the femur head in the acetabular implant. However ceramic inserts are relatively expensive. It can thus be preferred to use them for young patients only. For older patients, it can be preferred to use inserts made of polyethylene, which although it presents less resistance to wear, is less expensive.

Nevertheless, that solution is not satisfactory. The metal cup and the polyethylene insert are assembled by being impacted, with the shell presenting a conical bearing surface associated with various fastener means. However the insert is not held sufficiently firmly in the cup. There remains the possibility of micromovements between those two parts. Such micromovements cause particles of polyethylene to become detached which then penetrate into the holes for the screws and come into contact with bone. That leads to osteolyses, and in the long run to the acetabulum separating due to degradation of the bone-metal contact surface.

The object of the invention is to propose a novel configuration for an acetabular implant for a total hip prosthesis, allowing a polyethylene insert to be used in association with a metal cup, but without the above-mentioned drawbacks.

To this end, the invention provides an acetabular implant cup insert for a joint prosthesis, the insert being of the type comprising a metal shell and a polymer lining the inside space of said shell, a receptacle for a prosthetic head being formed in the lining, said shell presenting on its inside space means for preventing said lining being extracted from the shell and means for preventing the lining turning in the shell, the insert being characterized in that said means for preventing the lining being extracted comprise a stud disposed on the end wall of the shell and presenting at least one groove or lip.

Said means for preventing extraction of said lining may include at least one lip.

Said means for preventing said lining may be extracted include at least one groove.

Said means for preventing the lining from turning may comprise projections formed on the surface of the wall defining the inside space of the shell.

Said projections may be ribs extending over all or a fraction of the height of the inside space of the shell.

Said means for preventing the lining from turning may comprise depressions formed in the surface of the wall defining the inside space of the shell.

Projections may be formed on the lip.

Depressions may be formed in the lip.

The anterior portion of said shell may present a conical shape.

The wall of the receptacle may be covered in ceramic.

Said lining may be obtained by an operation of thermocompressing said polymer in said inside space of the shell, followed by a machining operation.

Said lining may be obtained by prior shaping, and it may be put into place by being impacted into the shell.

The invention also provides an acetabular implant of the type comprising a cup for being fastened in the pelvis or a shoulder blade of a patient, and an insert lining the inside of said cup in order to receive a prosthetic head, the implant being characterized in that the insert is of the above type.

The invention also provides a joint prosthesis of the type comprising an acetabular implant and a prosthetic head, the prosthesis being characterized in that said implant is of the above type.

As will have been understood, the invention consists firstly in providing an insert made up of two parts:
  a basic metal shell; and
  a polyethylene part.

Anchor means, such as peripheral and transverse lips, and/or grooves formed in the metal shell, ensure that the polyethylene is held completely stationary relative to the metal. This avoids any rubbing that might cause particles of polyethylene to be released into the environment of the insert.

According to the invention, the essential element of said anchor means is a stud formed on the end wall of the shell, and presenting a groove or a lip.

The invention can be better understood on reading the following description given with reference to the accompanying figures, in which:

FIG. 1 is a side view (FIG. 1a) and a plan view (FIG. 1b) of an example of a metal shell for forming part of an acetabular implant insert of the invention; and FIG. 2 is a partially cutaway diagrammatic perspective view showing the metal and polymer elements separately of an embodiment of an acetabular implant insert of the invention.

The metal shell 1 (generally made of stainless steel or titanium) presents an outside shape that is frustoconical (in the example shown) or spherical in its posterior portion 2, and a shape that is substantially cylindrical in its anterior portion 3. Preferably, and as shown, the anterior portion 3 is slightly conical which, when the cup is in place in the patient's pelvis or shoulder blade, contributes to holding the shell 1 in place. The shell 1 is designed to be put into place in a metal acetabulum (not shown), itself secured to the patient's pelvis or shoulder blade by cement or screws.

The inside space 4 of the shell 1 in the example shown is frustoconical in shape in its posterior portion 5 and cylindrical in shape in its anterior portion 6. In a variant, these shapes could be respectively spherical (for example) and frustoconical.

The anterior portion 6 of the inside space 4 of the shell 1 presents an inwardly-projecting lip 7 around its periphery, the lip itself being provided with depressions 8 and projections 9. Furthermore, according to the invention, the end wall 10 of the posterior portion 5 of the inside space 4 of the shell 1 presents a stud 11 of substantially cylindrical shape, having a side wall that includes a groove 12 (as shown), and/or a lip in relief, or a plurality of such grooves 12 and/or of such lips.

In an embodiment, in order to obtain an acetabular implant insert of the invention, a metal shell of the type described above is made initially. Then its inside space is filled with polyethylene (or some other polymer suitable for making this type of implant) by a thermocompression method, i.e. by being injected hot and under pressure. The polyethylene is caused to overflow from the top edge 13 of the shell 1. Thereafter, the polyethylene lining 14 as obtained in this way is machined so as to give it a shape suitable for enabling it to receive the head of the hip or shoulder prosthesis of which the acetabular implant of the invention forms a part.

FIG. 2 shows the shell 1 and its polyethylene lining 14 after it has been machined. It should be understood that these two elements are shown separately only for convenience in the figure, and that in reality, in this embodiment, the lining 14 remains permanently in the shell 1. The specific function of the lip 7 in relief is to prevent the lining 14 from being extracted after it has been made, in particular while the implant of the invention is in use. During the thermocompression operation, a groove 15 is formed in the outer periphery of the lining 14 in register with the lip 7. The lip 7 thus penetrates into the lining and prevents any movement of the lining 14 tending to extract it from the shell 1.

The stud 11 performs a similar function. During thermocompression, the polyethylene becomes molded around it, and the presence of the groove 12 (or of a lip) enables the lining 14 to remain held to the stud 11 by forming a lip 16 in relief (or a groove) on or in the lining 14 in register with the groove 12 (or the lip) of the stud 11. The presence of this stud 11 provides entirely effective resistance against the lining 14 being extracted and adds to the effect of the other anti-extraction elements. It could even, optionally, constitute the only anti-extraction element.

The depressions 8 and the projections 9 formed in and on the lip 7 prevent the lining 14 from turning inside the shell 1.

In this way, any movement of the lining 14 in the shell 1 is prevented with optimum effectiveness in all directions in three-dimensional space. This ensures that no such movement leads to any displacement or erosion of the lining 14.

Other than for the stud 11, the configuration as described and shown for the means that prevent the lining 14 from moving in the shell 1 and out from the shell 1 is merely an example.

The lip 7 may be continuous around the entire periphery of the inside space 4 of the shell 1, or it may be discontinuous. There may be a plurality of rings distributed over different levels of the inside space 4 of the shell 1. They could be replaced by one or more grooves creating corresponding relief on the lining 14 during thermocompression. Nevertheless, the lip 7 is the preferred configuration for the anti-extraction means other than the stud 11. After thermocompression, polyethylene is the subject of 1.8% shrinkage. This shrinkage tends to reinforce the connection between the lining 14 and the shell 1 when the shell presents a lip 7, whereas a groove would tend to weaken the connection. Naturally, both lips and grooves can be combined. This effect of strengthening the connection by the polyethylene shrinking is also very perceptible at the stud 11, and specifically the shape of the stud 11 enables good advantage to be taken of this effect.

Concerning the means that prevent rotation, it is possible to provide only depressions 8 or only projections 9, and to provide them at locations other than the lip 7 on the surface of the wall defining the inside space 4 of the shell 1. For the same reason as above, to do with polyethylene shrinking, the projections 9 are of greater importance. They may be in the form of ribs extending over all or a fraction of the height of the inside space 4 of the shell 1.

As can be seen in FIG. 2, the machining applied to the lining 14 after thermocompression serves firstly to provide a rim 17 resting on the top edge 13 of the shell 1, and above all a receptacle 18 of spherical shape for receiving heads of various materials (ceramics or metals) belonging to the hip or shoulder prosthesis of which the acetabular implant of the invention is to form a part.

In a variant, it is possible also to incorporate a ceramic lining in the receptacle 18, in particular by thermocompression. In this way, the contact between the insert and the head of the prosthesis, if the head is made of ceramic, is ceramic-on-ceramic contact, thereby avoiding any release of polyethylene into the environment of the prosthesis.

In another embodiment, the lining 14 is made, not by thermocompression in the shell 1, but by a shaping operation (molding and/or machining, for example) that is performed outside the shell 1. Thereafter the lining 14 is put into place inside the shell 1 by being impacted into the shell 1, with the lining 14 presenting recessed and projecting portions complementary to the projecting and recessed portions presented by the inside space 4 of the shell 1. Optionally, where necessary, a final machining operation on the lining 14 after it has been put into place can serve to adjust its outside dimensions. In this case also, a ceramic coating may be added in the receptacle 18.

The invention claimed is:

1. An acetabular implant cup insert for a joint prosthesis, the insert comprising:
   a metal shell;
   a polymer lining lining an inside space of said shell; and
   a receptacle for a prosthetic head being formed in the lining, said shell presenting on said inside space of the shell means for preventing said lining being extracted from the shell and means for preventing the lining turning in the shell,
   wherein said means for preventing the lining being extracted comprise a stud disposed on an end wall of a posterior portion of the inside space of the shell,
   said stud having at least one groove or lip with which the lining interfits to lock the lining on the shell, and
   said stud and said shell are of one piece and integrally formed.

2. The insert according to claim 1, wherein said means for preventing extraction of said lining include at least one lip.

3. The insert according to claim 1, wherein said means for preventing said lining being extracted include at least one groove.

4. The insert according to claim 1, wherein said means for preventing the lining from turning comprise projections formed on the surface of the wall defining the inside space of the shell.

5. The insert according to claim 4, wherein said projections are ribs extending over all or a fraction of the height of the inside space of the shell.

6. The insert according to claim 1, wherein said means for preventing the lining from turning comprise depressions formed in the surface of the wall defining the inside space of the shell.

7. The insert according to claim 1, wherein the anterior portion of said shell presents a conical shape.

8. The insert according to claim 1, wherein the wall of the receptacle is covered in ceramic.

9. The insert according to claim 1, wherein said lining is obtained by an operation of thermocompressing said polymer in said inside space of the shell, followed by a machining operation.

10. The insert according to claim 1, wherein said lining is obtained by prior shaping, and wherein it is put into place by being impacted into the shell.

11. The insert according to claim 1, wherein said stud is disposed centrally of the shell.

12. The insert according to claim 1, wherein the insert is a polymer cast within the shell.

13. The insert according to claim 12, wherein the polymer and the shell have interfitting portions permanently interlocking the cast polymer lining within the shell.

14. An acetabular implant cup insert for a joint prosthesis, the insert comprising:
- a metal shell;
- a polymer lining lining an inside space of said shell; and
- a receptacle for a prosthetic head being formed in the lining, said shell presenting on the inside space of said shell means for preventing said lining being extracted from the shell and means for preventing the lining turning in the shell,
- wherein said means for preventing the lining being extracted comprise a stud disposed on an end wall of a posterior portion of the inside space of the shell,
- said stud having at least one groove or lip with which the lining interfits to lock the lining on the shell,
- said means for preventing extraction of said lining includes at least one lip,
- said means for preventing the lining from turning comprise projections formed on the surface of the wall defining the inside space of the shell, and
- projections are formed on the lip.

15. An acetabular implant cup insert for a joint prosthesis, the insert comprising:
- a metal shell;
- a polymer lining lining an inside space of said shell,
- a receptacle for a prosthetic head being formed in the lining, said shell presenting on the inside space of said shell means for preventing said lining being extracted from the shell and means for preventing the lining turning in the shell,
- wherein said means for preventing the lining being extracted comprise a stud disposed on an end wall of the posterior portion of the inside space of the shell,
- said stud having at least one groove or lip with which the lining interfits to lock the lining on the shell,
- said means for preventing extraction of said lining includes at least one lip,
- said means for preventing the lining from turning comprise depressions formed in the surface of the wall defining the inside space of the shell, and
- depressions are formed in the lip.

16. An acetabular implant comprising a cup for being fastened in the pelvis or a shoulder blade of a patient, and an insert lining the inside of said cup in order to receive a prosthetic head, wherein the insert is according to claim 1.

17. A joint prosthesis comprising an acetabular implant and a prosthetic head, wherein said implant is according to claim 2.

* * * * *

UNITED STATES PATENT AND TRADEMARK OFFICE
CERTIFICATE OF CORRECTION

PATENT NO. : 8,556,984 B2  Page 1 of 1
APPLICATION NO. : 10/559680
DATED : October 15, 2013
INVENTOR(S) : Serge Calamel It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1231 days.

Signed and Sealed this
Fifteenth Day of September, 2015

Michelle K. Lee
*Director of the United States Patent and Trademark Office*